(12) United States Patent
Tsai et al.

(10) Patent No.: US 7,795,473 B2
(45) Date of Patent: Sep. 14, 2010

(54) SYSTEM AND METHOD FOR PREPARING CYCLOALKANONE

(75) Inventors: Yau-Ching Tsai, Taipei (TW); Chih-Chung Chou, Taipei (TW); Chin-Hisang Lin, Taipei (TW)

(73) Assignee: China Petrochemical Development Corporation, Taipei (TW)

( * ) Notice: Subject to any disclaimer, the term of this patent is extended or adjusted under 35 U.S.C. 154(b) by 0 days.

(21) Appl. No.: 12/424,714

(22) Filed: Apr. 16, 2009

(65) Prior Publication Data

US 2009/0264682 A1    Oct. 22, 2009

(30) Foreign Application Priority Data

Apr. 17, 2008  (TW)  ................. 97113894 A
Jun. 25, 2008  (TW)  ................. 97123647 A

(51) Int. Cl.
*C07C 45/27*   (2006.01)
*C07C 45/83*   (2006.01)

(52) U.S. Cl. ..................................... 568/366

(58) Field of Classification Search ................. 568/366; 422/211, 224

See application file for complete search history.

(56) References Cited

U.S. PATENT DOCUMENTS 4,326,085 A    4/1982    De Cooker

*Primary Examiner*—Sikarl A Witherspoon
(74) *Attorney, Agent, or Firm*—Peter F. Corless; Steven M. Jensen; Edwards Angell Palmer & Dodge LLP

(57) ABSTRACT

A system and a method for preparing cycloalkanone are provided. The method includes the steps of: (a) oxidizing cycloalkane to form a mixture containing ketone, alcohol and unreacted cycloalkane; (b) adding to the mixture alkali metal hydroxide or alkali metal carbonate to form a first mixed solution; (c) separating the first mixed solution into a first organic phase solution and a first aqueous phase solution; and (d) extracting the first organic phase solution by water to obtain a second organic phase solution and a second aqueous phase solution; and (e) distilling the second organic phase to separate out cycloalkanone. The method performs phase separation after a mixing step, and then performs water extraction, thereby effectively lowering the contents of the metal salts in the organic phases. Compared with acid-water extraction, the method not only provides better cooling effects but also reduces equipment corrosion, and therefore has the advantage of decreasing the need for sewage treatments.

14 Claims, 1 Drawing Sheet

SYSTEM AND METHOD FOR PREPARING CYCLOALKANONE

FIELD OF THE INVENTION

The present invention relates to systems and methods for preparing cycloalkanone, and more particularly, to a system and a method for preparing cyclohexanone by cycloalkane as a raw material.

DESCRIPTION OF RELATED ART

Cyclohexanone is not only an important starting material for preparing caprolactam (CPL), but also an important source for synthesizing chemical products such as nylon 6, nylon 6.6, etc. Thus, cyclohexanone plays an extremely important role in the organic chemical industry. Commonly observed industrial preparations of cyclohexanone use cyclohexane as a raw material, and after sequential steps of oxidization, neutralization, decomposition, etc. are performed, purification is carried out to obtain cyclohexanone.

In the presence of an oxygen-containing gas, the oxidized solution of cyclohexane contains other by-products such as monoacids, diacids, organic sodium salts, oxygen-containing aldehydes, esters, and complex organic substances with other unknown composition, in addition to cyclohexanol and cyclohexanone as primary products. Since such by-products are difficult to be removed during the latter stages of a caprolactam preparation and draw quality is severely affected when caprolactam contains aldehyde/ester, sodium hydroxide or sodium carbonate is often added in caprolactam preparations.

However, the organic mixture pumped out from the bottom of a saponification/mixing tank after completion of the above-mentioned reactions are directly delivered to an extraction tower to perform salt extraction, during which high concentrations of organic sodium salts are removed from the processing liquor to avoid formation of high molecular substances by condensation in drying and distilling areas due to the presence of sodium salts and high temperature environments. During extraction, if the amount of eluent is insufficient, the organic phase at the top of the extraction tower will contain excessive amounts of sodium salts. On the other hand, if a large amount of eluent is applied, not only does the effects on lowering the sodium salts are limited but also causes issues related to sewage treatment. Generally speaking, if large amounts of sodium salts exist in the organic phase after leaving the extraction tower, high molecular substances are likely to be generated and subsequently affect the production cost and capacity of caprolactam.

U.S. Pat. No. 4,326,085 discloses a method for eliminating by-products of cyclohexanone. In this method, the amount of sodium salts contained in the organic phase is reduced by neutralization and extraction with acidulous water as well as acetic acid solution. Nevertheless, extraction by acidic solutions used in this method not only increases sewage treatments but also causes equipment corrosions and adverse effects on lowering the temperature of the mixed solution.

Accordingly, it is desired to provide a simple method for effectively reducing the content of alkali metal sodium in an organic phase.

SUMMARY OF THE INVENTION

Therefore, the present invention provides a method for preparing cycloalkanone, comprising the steps of: (a) oxidizing cycloalkane having 5 to 12 carbon atoms to form a mixture comprising ketone, alcohol and unreacted cycloalkane; (b) adding to the mixture alkali metal hydroxide or alkali metal carbonate to form a mixed solution; (c) separating the mixed solution into a first organic phase solution comprising 25 to 45 wt % of cycloalkanone, 15 to 35 wt % of cycloalkanol, 1 to 20 wt % of water, and 100 to 20000 ppm of alkali metal ions, based on a total weight of the first organic phase solution, and a first aqueous phase solution; (d) extracting the first organic phase by water to form a second organic phase solution comprising 30 to 50 wt % of cycloalkanone, 20 to 40 wt % of cycloalkanol, 1 to 7 wt % of water and less than 80 ppm of the alkali metal ions, based on a total weight of the second organic phase solution, and a second aqueous phase solution having a alkalinity of from 100 to 2000 meq/kg; and (e) distilling the second organic phase to separate out the cycloalkanone.

The present invention also provides a system for preparing cycloalkanone, comprising an oxidization unit for allowing cycloalkane to be in contact with an oxygen-containing gas for carrying out an oxidization reaction, to form a mixture comprising ketone, alcohol and unreacted cycloalkane; a mixing unit for mixing alkali metal hydroxide or alkali metal carbonate with the mixture to form a mixed solution; a separation unit for separating the mixed solution into a first organic phase solution comprising 25 to 45 wt % of cycloalkanone, 15 to 35 wt % of cycloalkanol, 1 to 20 wt % of water and 100 to 20000 ppm of alkali metal ions, based on a total weight of the first organic phase solution, and a first aqueous phase solution; an extraction unit for using water to extract the first organic phase solution to form a second organic phase solution comprising 30 to 50 wt % of cycloalkanone, 20 to 40 wt % of cycloalkanol, 1 to 7 wt % of water and less than 80 ppm of alkali metal ions, based on a total weight of the second organic phase solution, and a second aqueous phase solution having an alkalinity of 100 to 2000 meq/kg; and a distillation unit for separating cycloalkanone from the second organic phase solution.

In accordance with the present invention, after the mixing step, a phase separation of an organic phase and an aqueous phase is performed, and then extraction is carried out by using water, thereby effectively lowering the contents of metal salts, particularly sodium salts, in the organic phase.

In the method of the present invention, phase separation of organic and aqueous phases is carried out successively after the step of mixing the mixture with an alkali metal base solution, and thereafter, the organic phase solution is extracted with water. It is found that the alkali metal salts in the organic phase solution can be effectively eliminated, especially sodium salts. Compared with acid-water extraction, the method of the present invention not only provides better cooling effects but also reduces equipment corrosion, and therefore has the advantage of decreasing the need for sewage treatments.

BRIEF DESCRIPTION OF THE DRAWINGS

The present invention can be more fully understood by reading the following detailed description of the preferred embodiments, with reference made to the accompanying drawings, wherein.

DETAILED DESCRIPTION OF THE PREFERRED EMBODIMENTS

Figure 1:
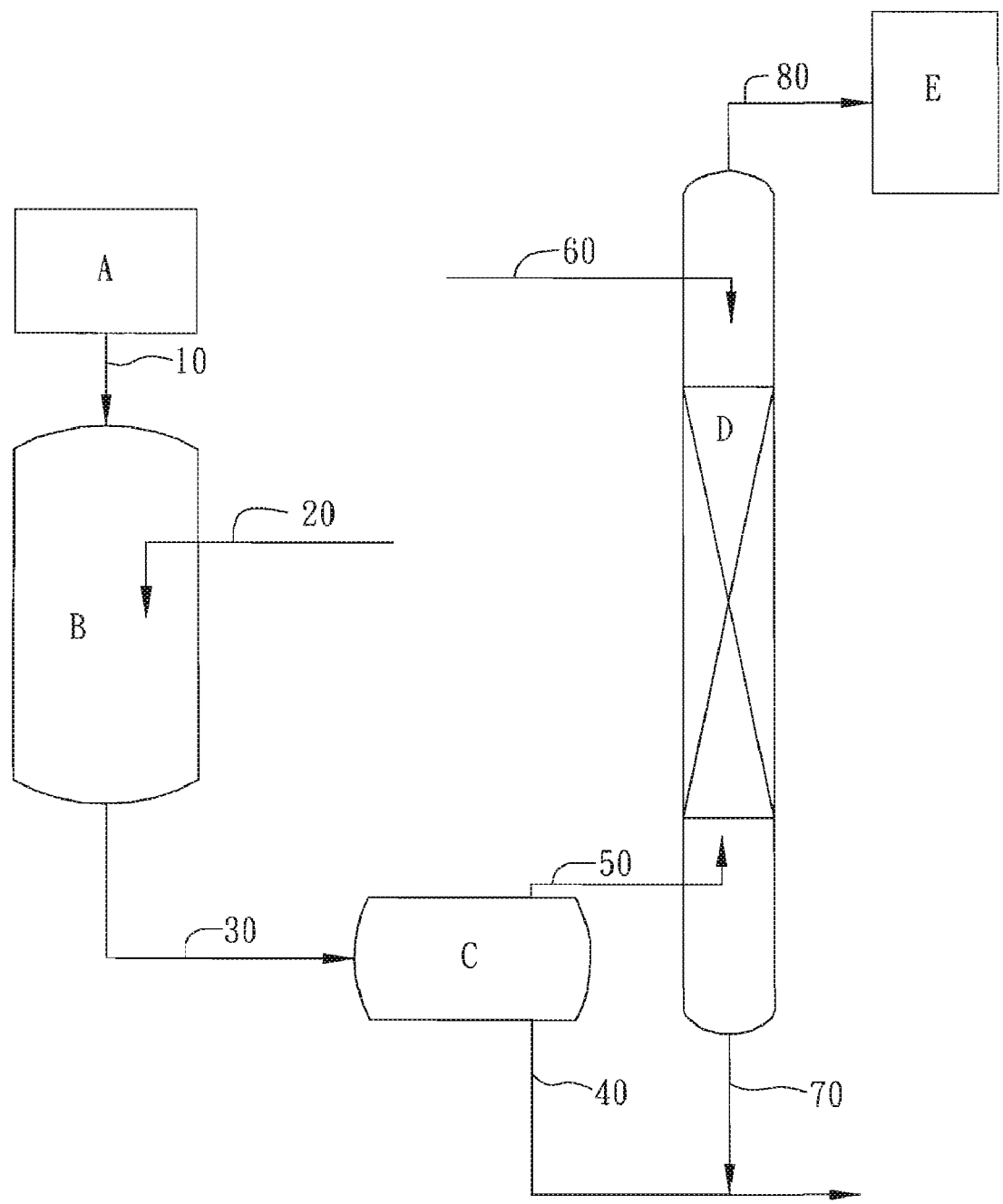
FIG. 1 is a schematic diagram showing a system for preparing cycloalkanone according to the present invention.

In the method for preparing cycloalkanone according to the present invention, cycloalkane having 5 to 12 carbon atoms is used as starting material to undergo an oxidization reaction with an oxygen-containing gas, so as to form an oxidized mixture containing cycloalkanone, cycloalkanol, unreacted cycloalkane, and other by-products. Examples of the by-products include, but not limited to, oxygen-containing aldehydes, esters, monoacids, diacids, and other organic impurities. In a preferred embodiment, cyclohexane is used as a raw material to be subjected to an oxidization reaction as to form the mixture having cyclohexanone, cyclohexanol, cyclohexyl peroxide, other acid-containing by-products or derivatives thereof, and unreacted cyclohexane. Generally speaking, the unreacted cyclohexane is not more than 50 wt %, preferably not more than 30 wt %, more preferably not more than 20 wt %, and further preferably not more than 10 wt %, based on the total weight of the mixture.

After the completion of the oxidization reaction, catalysts can be applied to decompose cyclohexyl peroxide present in the mixture, and a base solution is added to the mixture for carrying out saponification remove aldehydes and esters from the mixture before extraction and distillation to separate out cyclohexanone from the oxidized mixture. In the embodiment, the steps of decomposition and saponification are carried out before adding to the mixture alkali metal hydroxide to form a mixed solution containing an organic phase solution and an aqueous phase solution. The mixed solution is retained in a separating device for at least 1 minute, preferably 4 minutes and more preferably 6 minutes, for a first aqueous phase solution and a first organic phase solution to be separated from the mixed solution. It should be noted that considering production efficiency, the retention time of the mixed solution in the separating device should be less than 10 minutes, preferably less than 8 minutes, and more preferably less than 5 minutes. Examples of the separating device include, but not limited to, a retention/separation tank, a horizontal separation tank, and a separation tank packed with Rasching rings, etc. Based on the total weight of the first organic phase solution, the first organic phase solution obtained from the separating device typically comprises 25 to 45 wt %, and preferably 30 to 40 wt %, of cyclohexanol; 15 to 35 wt %, and preferably 20 to 30 wt %, of cyclohexanol; 1 to 20 wt %, and preferably 1 to 10 wt %, of water; and 100 to 20000 ppm, preferably 500 to 2000 ppm of alkali metal ions.

Examples of alkali metal hydroxide or alkali metal carbonate used in the present method include, but not limited to, potassium hydroxide, sodium hydroxide, sodium carbonate, etc. Alkali metal hydroxide, for example, sodium hydroxide, can be added in the form of an aqueous solution. Generally speaking, the alkalinity of an aqueous sodium hydroxide solution used is greater than 800 meq/kg, preferably greater than 1000 meq/kg, and more preferably more than 1200 meq/kg. On the other hand, to avoid aldehydes and esters in the mixed solution to condense and cause a lower yield of cyclohexanone due to incompletion of subsequent steps, the alkalinity of the aqueous sodium hydroxide solution used is usually less than 1800 meq/kg, preferably less than 1600 meq/kg, and more preferably less than 1500 meq/kg. In this embodiment, the amount of the base added is no more than 5 wt %, preferably no more than 3 wt %, and more preferably not more than 1 wt %, based on the weight of the mixed solution. While alkali metal hydroxide or alkali metal carbonate is added, the temperature of the mixed solution may be in the range of 85 to 100°, and preferably in the range of 90 to 98° C.

According to the present method, water is used to extract the first organic phase solution, so as to remove the metal salts, especially alkali metal salts such as potassium salts, sodium salts, etc., from the first organic phase solution, to further form a second organic phase solution and a second aqueous phase solution from the first organic phase solution. After separation, based on the total weight of the second organic phase solution, the second organic phase solution comprises 30 to 50 wt %, and preferably 35 to 45 wt %, of cyclohexanol; 20 to 40 wt %, and preferably 30 to 35 wt %, of cyclohexanol; 1 to 7 wt % of water, and preferably 1 to 5 wt % of water; and less than 80 ppm, and preferably less than 40 ppm, and more preferably less than 20 ppm, of alkali metal ions. Afterwards, the second organic phase is distilled to separate out cyclohexanone.

According to the method of the present invention, it is not necessary to use a large amount of eluant in the extraction process to achieve effective reduction in the alkali metal salts present in the second organic phase solution. Moreover, the alkalinity of the second aqueous phase solution after extraction is in the range of 100 to 2000 meq/kg, and preferably in the range of 500 to 1500 meq/kg, and thus the second aqueous phase not only can be recycled and reused but also avoid equipment corrosion due to use of acid-water extraction. Compared with common commercial preparations, the method of the present invention comparatively decreases about 20 to 30% of the eluant used, thereby effectively decreasing contents of alkali metal salts in the organic phases after extraction. For example, in the case of using an aqueous sodium hydroxide solution, after extraction, the sodium content in the second organic phase can be less than 50 ppm, preferably less than 10 ppm, and more preferably less than 5 ppm. Consequently, production costs of cyclohexanone can be decreased, thereby increasing the overall production capacity of caprolactam.

FIG. 1 is a schematic diagram showing a system for preparing cycloalkanone according to the present invention. Referring to FIG. 1, the system for preparing cycloalkanone according to the present invention comprises an oxidization unit A, a mixing unit B, a separation unit C, an extraction unit D and a distillation unit E. The oxidization unit A is primarily used for allowing cycloalkane having 5 to 12 carbon atoms to undergo oxidization with an oxygen-containing gas to form an oxidized mixture containing ketone, alcohol, unreacted cycloalkane, and the other by-products. In one embodiment, cyclohexane is used as a raw material for oxidization to form a reaction mixture of cyclohexanone, cyclohexanol, cyclohexyl peroxide, other acid by-products and derivatives thereof, and unreacted cyclohexane. Generally speaking, the unreacted cyclohexane is of less than 50 wt %, preferably less than 30 wt %, more preferably less than 20 wt %, and further preferably less than 10 wt %, based on the total weight of the mixture.

In this embodiment, the reaction mixture formed in the oxidization unit A may first undergoes saponification, and is then delivered to the mixing unit B via a pipeline 10. In the mixing unit B, the mixture after oxidization and saponification is further mixed with alkali metal hydroxide (such as potassium hydroxide, sodium hydroxide) or alkali metal carbonate (such as sodium carbonate) delivered to the mixing unit B via a pipeline 20, to form a mixed solution at a temperature of from 85° C. to 100° C., and preferably 90° C. to 98° C. Then, the mixed solution is fed to the separation unit C via a pipeline 30 by pumping. Alkali metal hydroxide such as sodium hydroxide can be added in the form of an aqueous solution into the mixing unit B via the pipeline 20. Generally speaking, the alkalinity of the aqueous sodium hydroxide solution used is more than 800 meq/kg, preferably more than 1000 meq/kg, and more preferably more than 1200 meq/kg. On the other hand, in order to prevent aldehydes and the esters in the mixture from condensation and cause a lower yield of cyclohexanone due to incompletion of subsequent separating steps, the alkalinity of the aqueous sodium hydroxide solution is usually less than 1800 meq/kg, preferably less than 1600 meq/kg, and more preferably less than 1500 meq/kg. In this embodiment, the amount of aqueous sodium hydroxide solution added is no more than 5 wt %, preferably no more than 3 wt %, and more preferably not more than 1 wt %, based on the total weight of the mixture.

In the system of the present invention, a retention/separation tank, a horizontal separation tank or a separation tank packed with Rasching rings can be used as the separation unit C. After the mixed solution is fed to the separation unit C via the pipeline 30, it is retained therein for at least 1 minute, preferably at least 4 minutes, and more preferably at least 6 minute, so as to separate the mixed into a first aqueous phase solution and a first organic phase solution. On the other hand, considering the production efficiency, the retention time of the mixed solution in the separation unit C is not more than 10 minutes, preferably not more than 8 minutes, and more preferably not more than 5 minutes. The first organic phase solution generally comprises, based on the total weight of the first organic phase solution, 25 to 45 wt %, and referably 30 to 40 wt %, of cyclohexanone; 15 to 35 wt %, and preferably 20 to 30 wt %, of cyclohexanol; 1 to 20 wt % of water, and preferably 1 to 10 wt %, of water; and 100 to 20000 ppm, and preferably 500 to 2000 ppm, of alkali metal ions.

The first aqueous phase solution separated in the separation unit C is discharged via a pipeline 40, and delivered to the bottom of the extraction unit D via a pipeline 50. Deionized water for extraction is introduced into the extraction unit D, for example, an extraction tower, via a pipeline 60, and is in countercurrent contact with the first organic phase solution to perform water extraction. After extraction, a second aqueous phase solution is discharged from the bottom of the extraction unit D via a pipeline 70, and a second organic phase solution is discharged from the top of extraction unit D via a pipeline 80 to be delivered to the distillation unit E to further separate out cyclohexanone.

In this embodiment, the second organic phase solution separated from the top of extraction unit D comprises, based on the weight of the second organic phase solution, 30 to 50 wt %, and preferably 35 to 45 wt %, of cyclohexanone; 20 to 40 wt %, and preferably 30 to 35 wt %, of cyclohexanol; 1 to 7 wt %, and preferably 1 to 5 wt %, of water; and less than 80 ppm of alkali metal ion, preferably less than 40 ppm of alkali metal ion, and more preferably less than 20 ppm of alkali metal ions. The alkalinity of the second aqueous phase solution separated from the bottom of extraction unit D is in the range of 100 to 2000 meq/kg, and preferably in the range of 500 to 1500 meq/kg. This not only can recycle and reuse the aqueous phase solution, but also avoid equipment corrosion due to use of acid-water extraction. In the case of an aqueous sodium hydroxide solution added, the sodium content in the second organic phase separated from the top of the extraction unit D can be less than 50 ppm, preferably less than 10 ppm, and more preferably less than 5 ppm.

EXAMPLES

Example 1

Cyclohexane was used for oxidization with an oxygen-containing gas. An aqueous sodium hydroxide solution having alkalinity of 1350 meq/kg was added to the oxidized cyclohexyl mixture. The obtained mixture was pumped out at a flow rate of 26 $M^3$/hr from the bottom of the mixing tank, and was analyzed by a coulometric moisture meter and an atomic adsorption spectrometer. The water and sodium contents were 10.7 wt % and 1105 ppm, respectively.

The mixture was then delivered to a horizontal separation tank and retained for about 6 minutes before discharging the aqueous phase and delivering the organic phase to the bottom of the extraction tower. The organic phase was analyzed. The analysis showed that the organic phase contained 35.4 wt % of cyclohexanone, 25.1 wt % of cyclohexanol, 5 wt % of water, and 850 ppm of sodium ion. Deionized water was delivered to the extraction tower at a flow rate of 9 $M^3$/hr to perform countercurrent extraction, during which the deionized water flowed in a direction opposite to the flow of the organic phase. After extraction, the organic solution was analyzed to obtain a result showing that the organic solution contains 41.3 wt. % of cyclohexanone, 31 wt % of cyclohexanol, 3.2 wt % of water, and 4.7 ppm of sodium ions. Finally, the organic solution was delivered to a distillation tower to separate out cyclohexanone.

Example 2

Cyclohexane was used for oxidization with an oxygen-containing gas. An aqueous sodium hydroxide solution having alkalinity of 1225 meq/kg was added to the oxidized cyclohexyl mixture. The obtained mixture was pumped out at a flow rate of 10 $M^3$/hr from the bottom of the mixing tank, and was analyzed by a coulometric moisture meter and an atomic adsorption spectrometer. The water and sodium contents were 14.1 wt % and 1624 ppm, respectively.

The mixture was then delivered to a horizontal separation tank and retained for about 4 minutes before discharging the aqueous phase and delivering the organic phase to the bottom of the extraction tower. The organic phase was analyzed. The analysis showed that the organic phase contained 36.2 wt % of cyclohexanone, 27.9 wt % of cyclohexanol, 4 wt % of water, and 230 ppm of sodium ion. Deionized water was delivered to the extraction tower at a flow rate of 6.8 $M^3$/hr to perform countercurrent extraction, during which the deionized water flowed in a direction opposite to the flow of the organic phase. After extraction, the organic solution was analyzed to obtain a result showing that the organic solution contains 40.8 wt. % of cyclohexanone, 29.5 wt % of cyclohexanol, 4.7 wt % of water, and 3.3 ppm of sodium ions. Finally, the organic solution was delivered to a distillation tower to separate out cyclohexanone.

Comparative Example 1

Cyclohexane was used for oxidization with an oxygen-containing gas. An aqueous sodium hydroxide solution having alkalinity of 1175 meq/kg was added to the oxidized cyclohexyl mixture. The obtained mixture was pumped out at a flow rate of 43 $M^3$/hr from the bottom of the mixing tank, and was analyzed by a coulometric moisture meter and an atomic adsorption spectrometer. The water and sodium contents were 12.4 wt % and 1250 ppm, respectively.

The mixture was then delivered to the bottom of the extraction tower. Deionized water was delivered to the extraction tower at a flow rate of 12 $M^3$/hr to perform countercurrent extraction. After extraction, the organic solution was analyzed to contain 37.6 wt. % of cyclohexanone, 29.5 wt % of cyclohexanol, 5.2 wt % of water, and 83 ppm of sodium ions. Finally, the organic solution was delivered to a distillation tower to separate out cyclohexanone.

The invention has been described using exemplary preferred embodiments. However, it is to be understood that the scope of the invention is not limited to the disclosed embodi-

What is claimed is:

1. A method for preparing cycloalkanone, comprising the steps of:
   (a) oxidizing cycloalkane having 5 to 12 carbon atoms to form a mixture comprising ketone, alcohol and unreacted cycloalkane;
   (b) adding to the mixture alkali metal hydroxide or alkali metal carbonate to form a mixed solution;
   (c) separating the mixed solution into a first organic phase solution comprising 25 to 45 wt % of cycloalkanone, 15 to 35 wt % of cycloalkanol, 1 to 20 wt % of water, and 100 to 20000 ppm of alkali metal ions, and a first aqueous phase solution, based on a total weight of the first organic phase solution;
   (d) extracting the first organic phase solution by water to form a second organic phase solution, comprising 30 to 50 wt % of cycloalkanone, 20 to 40 wt % of cycloalkanol, 1 to 7 wt % of water and less than 80 ppm of the alkali metal ions, based on a total weight of the second organic phase solution, and a second aqueous phase solution having an alkalinity of from 100 to 2000 meq/kg; and
   (e) distilling the second organic phase solution to separate out the cycloalkanone.

2. The method according to claim 1, wherein the cycloalkane is cyclohexane.

3. The method according to claim 1, wherein the alkali metal hydroxide is sodium hydroxide.

4. The method according to claim 1, wherein the alkali metal carbonate is sodium carbonate.

5. The method according to claim 1, wherein the alkali metal hydroxide or the alkali metal carbonate is added in a form of an aqueous solution in step (b).

6. The method according to claim 5, wherein the aqueous solution of the alkali metal hydroxide has an alkalinity of from 800 to 1800 meq/kg.

7. The method according to claim 1, wherein the step (b) is performed after saponification of the mixture.

8. The method according to claim 1, wherein step (c) is performed in a retention/separation tank.

9. The method according to claim 1, wherein step (c) is performed in a separation tank packed with a plurality of Rasching rings.

10. The method according to claim 1, wherein the step (c) is performed for at least 1 minute.

11. The method according to claim 1, wherein the first organic phase solution comprises 30 to 40 wt % of cyclohexanone, 20 to 30 wt % of cyclohexanol, 1 to 10 wt % of water and 500 to 20000 ppm of alkali metal ions, based on the total weight of the first organic phase solution.

12. The method according to claim 1, wherein the water used in step (d) is deionized water or recycled water from the method to extract the first organic phase solution.

13. The method according to claim 1, wherein the second organic phase comprises 35 to 45 wt % of cyclohexanone, 30 to 35 wt % of cyclohexanol, 1 to 5 wt % of water and less than 40 ppm of alkali metal ions, based on the total weight of the second organic phase solution.

14. The method according to claim 1, wherein the second organic phase solution has a sodium content of less than 50 ppm.

* * * * *